(12) United States Patent
Iriyama et al.

(10) Patent No.: US 6,374,025 B1
(45) Date of Patent: Apr. 16, 2002

(54) LIGHTGUIDE CONNECTOR JOINT IN AN ENDOSCOPIC SYSTEM

(75) Inventors: Kenichi Iriyama; Hideo Sugimoto, both of Tokyo (JP)

(73) Assignee: Asahi Kogaku Kogyo Kabushiki Kaisha, Tokyo (JP)

( * ) Notice: Subject to any disclaimer, the term of this patent is extended or adjusted under 35 U.S.C. 154(b) by 0 days.

(21) Appl. No.: 09/352,943

(22) Filed: Jul. 14, 1999

(30) Foreign Application Priority Data

Jul. 16, 1998 (JP) .......................................... 10-201649

(51) Int. Cl.[7] ................................................ G02B 6/06
(52) U.S. Cl. ........................................ 385/117; 385/116
(58) Field of Search ................................. 385/117, 116, 385/115, 119, 88, 89, 93, 90

(56) References Cited

U.S. PATENT DOCUMENTS

| | | | |
|---|---|---|---|
| 4,738,055 A | * 4/1988 | Jackson et al. | 451/28 |
| 4,909,990 A | * 3/1990 | Block et al. | 422/82.11 |
| 5,036,834 A | 8/1991 | Sugiyama et al. | |
| 5,170,454 A | * 12/1992 | Kanai | 385/88 |
| 5,237,403 A | 8/1993 | Sugimoto et al. | |
| 5,500,918 A | * 3/1996 | Pileski et al. | 385/117 |
| 5,522,006 A | * 5/1996 | Takeuchi et al. | 385/139 |
| 5,800,343 A | * 9/1998 | Takeuchi et al. | 600/132 |

* cited by examiner

Primary Examiner—Rodney Bovernick
Assistant Examiner—Sung Pak
(74) Attorney, Agent, or Firm—Greenblum & Bernstein, P.L.C.

(57) ABSTRACT

In a lightguide connector joint for an endoscopic system, the shape and dimensions of a lightguide connector (3) are determined in accordance with the size of the entrance end face (4a) of a lightguide (4) such that the smaller the size of the entrance end face (4a), the closer to the converging position of the rays of illuminating light is the position of the entrance end face (4a) that is established when the lightguide connector (3) is connected to a connector receptacle (20).

14 Claims, 6 Drawing Sheets

LIGHTGUIDE CONNECTOR JOINT IN AN ENDOSCOPIC SYSTEM

BACKGROUND OF THE INVENTION

The present invention relates to a lightguide connector joint for an endoscopic system, by which a lightguide connector of an endoscope is connected to a light source apparatus.

In general, an endoscope is equipped with an illumination light guide an illumination light entrance end face of which is disposed at a distal end face of a lightguide connector. A connector receptacle to which the lightguide connector is to be connected is provided in a light source apparatus having a built-in light source. When the lightguide connector is connected to the connector receptacle, the entrance end face of the lightguide is situated in a specified position near a position at which the rays of illuminating light radiated from the light source are converged.

Various endoscopes of the above-noted design are available depending on respective purposes and intended uses, and an operator can select one or ones from the various endoscopes in combination with a single light source apparatus to constitutes a desired endoscopic system. In the endoscopic system, a selected one of the endoscopes is connected to the light source apparatus depending on a specific purpose or use. However, the thickness of an endoscope's illuminating lightguide (or the number of optical fibers in it) varies with the endoscope model or type.

Some combinations are appropriate in that when the endoscope's lightguide connector is connected to the connector receptacle in the light source apparatus, the illuminating light is incident on the entrance end face of the lightguide to give neither surplus nor deficiency.

However, in a model of endoscope having a smaller entrance end face of lightguide than the appropriate model, a portion of the illuminating light fails to be incident on the lightguide and the efficiency of illumination is reduced. In other words, sufficiently bright illuminating light cannot be obtained even if a high-intensity light source is used.

Conversely, in a model of endoscope having a thicker entrance end face of lightguide than the appropriate model, a relatively small amount of illuminating light is incident in those areas of the lightguide which are far from the center and the object is illuminated unevenly.

SUMMARY OF THE INVENTION

The present invention has been accomplished under these circumstances and has as an object providing a lightguide connector joint for an endoscopic system which is compatible with various endoscope models using lightguides with different thickness of entrance end face and which ensures that the rays of illuminating light radiated from a light source are incident on the lightguide to cause neither surplus nor deficiency, thereby achieving satisfactory illumination with high efficiency.

The stated object of the invention can be attained by a lightguide connector joint for an endoscopic system in which the entrance end face of an endoscope's illuminating lightguide is disposed at the distal end face of a lightguide connector, and a connector receptacle to which said lightguide connector is to be connected is provided in a light source apparatus having a built-in light source. When said lightguide connector is connected to said connector receptacle, the entrance end face of said lightguide is situated near a position in which the rays of illuminating light radiated from said light source are converged. In the light guide connector joint, the shape and dimensions of said lightguide connector are determined in accordance with the size of the entrance end face of said lightguide such that the smaller the size of said entrance end face, the closer to the converging position of said rays of illuminating light is the position of said entrance end face that is established when said lightguide connector is connected to said connector receptacle.

If desired, said connector receptacle may be shaped in the form of a tapered hole that progressively decreases in diameter in a direction toward said light source whereas the tip portion of said lightguide connector is shaped in the from of a tapered rod that fits into said connector receptacle.

Another embodiment is such that when said lightguide connector is connected to said connector receptacle, a stopper formed on said lightguide connector contacts a reference positron formed on said connector receptacle side and that the distance from said position of contact to the entrance end face of said lightguide is determined in accordance with the size of said entrance end face.

In yet another embodiment, a ventilation window for cooling the distal end portion of said lightguide connector is provided in a lens unit incorporating a lens for converging the rays of illuminating light radiated from said light source. If desired, a cooling fan may be provided in the ventilation window.

The present disclosure relates to the subject matter contained in Japanese patent application No. Hei. 10-201649 (filed on Jul. 16, 1998), which is expressly incorporated herein by reference in its entirety.

DESCRIPTION OF THE PREFERRED EMBODIMENT

Preferred embodiments of the invention are hereunder described with reference to the accompanying drawings.

Figure 3:
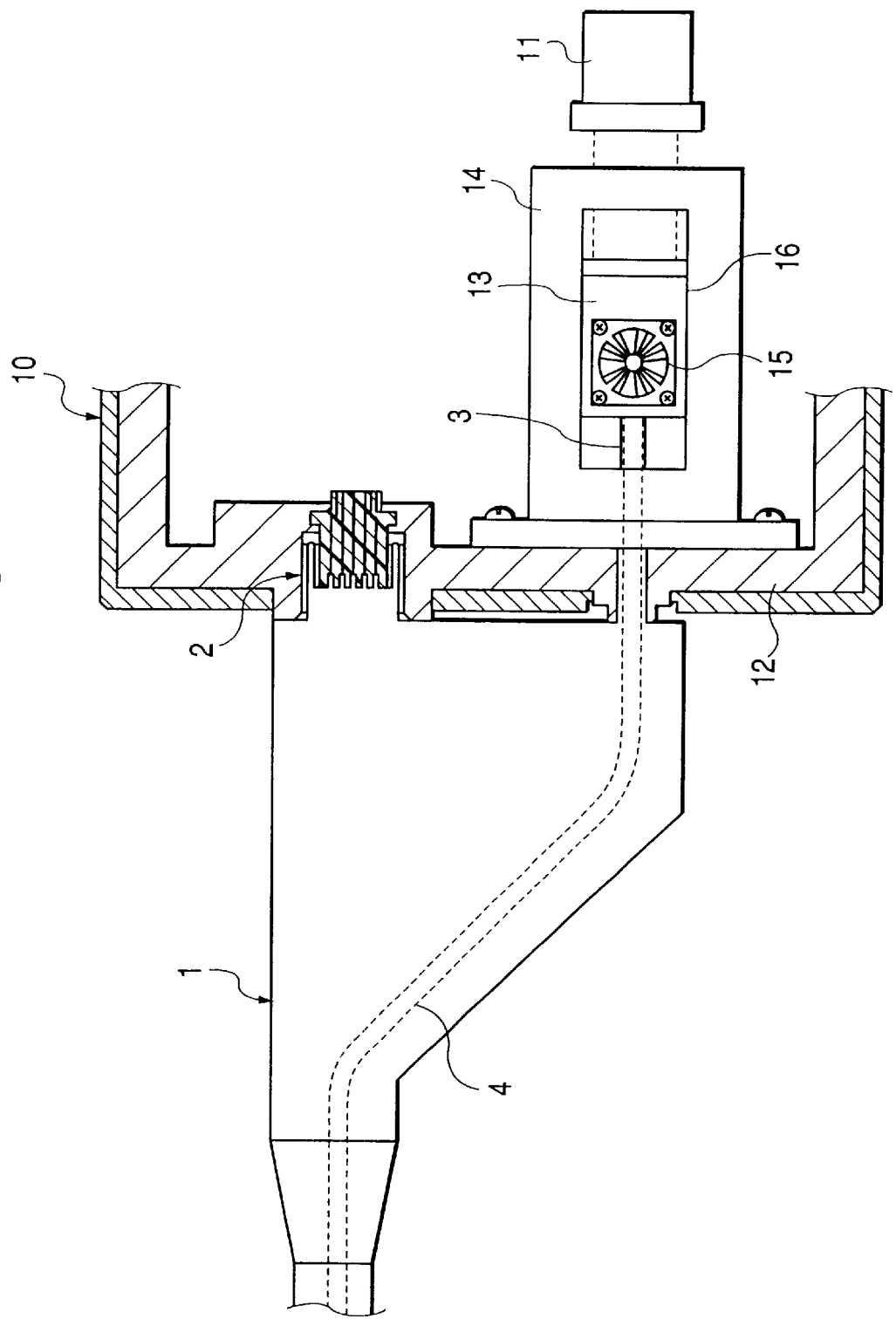
FIG. 3 is a side sketch of a lightguide connector joint for an endoscopic system according to the first embodiment of the invention.

FIG. 3 shows the joint between the connector portion 1 of an endoscope and a light source apparatus 10.

The connector portion 1 can be attached to or detached from the light source apparatus 10. If attached to the light source apparatus 10, the connector portion 1 permits simultaneous connection with a connector 2 for transmission of electrical signals and a lightguide connector 3.

If an electronic endoscope is connected, picture signals or the like that are captured with a solid-state imaging device are transmitted through the connector 2. If an optical endoscope is connected, signals for shooting with automatic exposure and the like are transmitted through the connector 2.

The lightguide connector 3 is of such a design that the rays of illuminating light radiated from a lamp 11, i.e. the light source, that is fixed to the frame 12 of the light source apparatus 10 are emitted into an endoscope's illuminating lightguide fiber bundle 4.

The lightguide connector 3 is formed as a rod that projects from an end of the connector portion 1. The distal end of the lightguide connector 3 is adapted to be inserted into a light condensing cylinder 13 provided within the light source apparatus 10.

The light condensing cylinder 13 is provided within a support cylinder 14 fixed to the frame 12 of the light source apparatus 10 and its interior is cooled with a cooling fan 15 attached to its side. A ventilation window 161 large enough to allow effective cooling is made in the side wall of the support cylinder 14.

Figure 4:
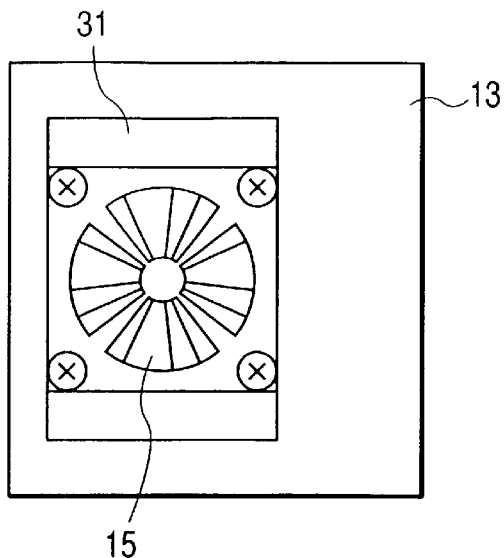
FIG. 4 is a partial side view of the first embodiment of the invention.
Figure 5:
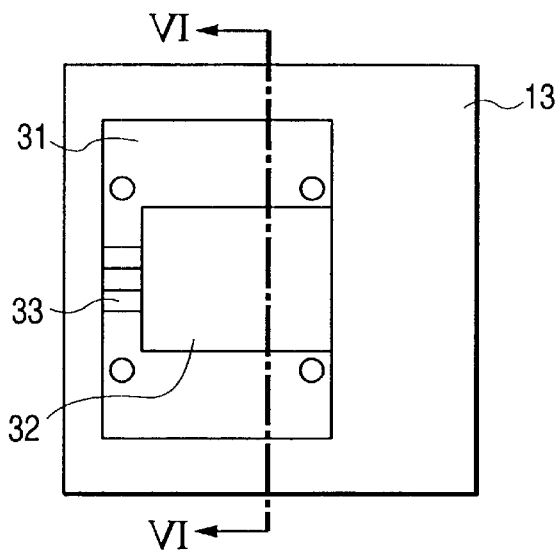
FIG. 5 is a side view, with part taken away, of the first embodiment of the invention.
Figure 6:
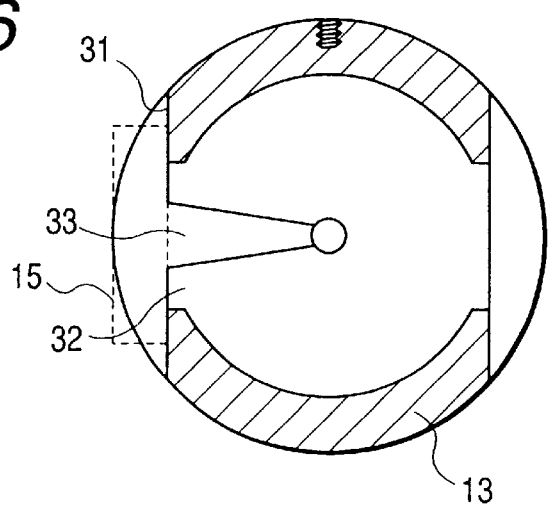
FIG. 6 is section VI—VI of FIG. 5.

The light condensing cylinder 13 is shown in an enlarged manner in FIG. 4. A fan mounting portion 31 on which the cooling fan 15 is to be mounted is formed on a lateral side of the light condensing cylinder 13. FIG. 5 shows the light condensing cylinder 13 with the cooling fan 15 dismounted. FIG. 6 is section VI—VI of FIG. 5. As these figures show, a ventilation hole 32 penetrating the side wall of the light condensing cylinder 13 is formed in a position somewhat close to the center of the fan mounting portion 31.

A ventilation groove 33 is formed in the front end wall of the light condensing cylinder 13 in such a way that it leads to the forward end of the lightguide connector 3. With this construction, if the cooling fan 15 is driven, an air stream outside the support cylinder 14 is aspirated into the light condensing cylinder 13, from which it is flowed to the lightguide connector 3 to prevent it from being overheated.

Figure 1:
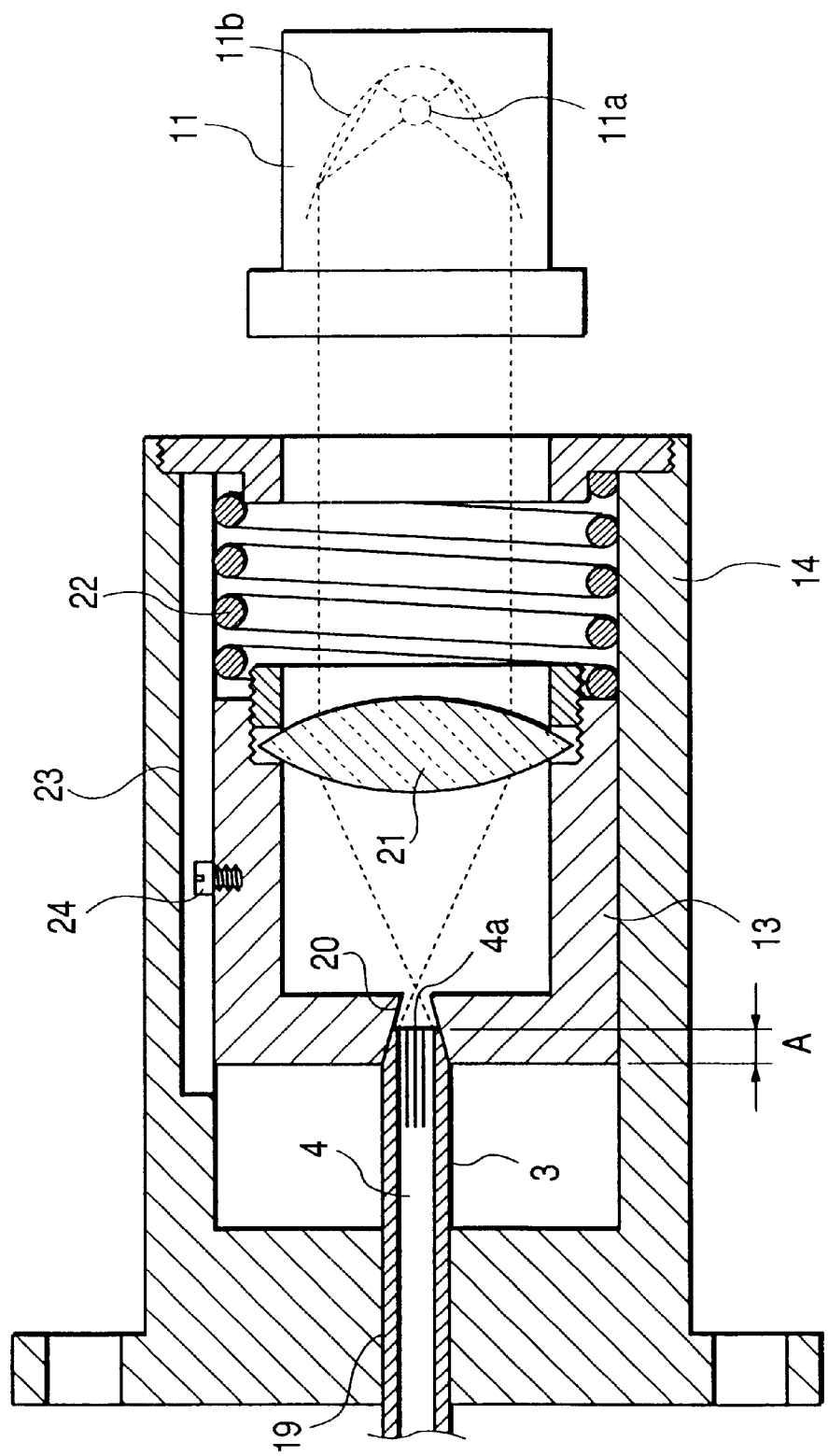
FIG. 1 is a longitudinal section of a joint between an endoscope's lightguide connector and a light source apparatus according to a first embodiment of the invention.

FIG. 1 shows, in an enlarged manner, the joint between the lightguide connector 3 and the light source apparatus 10.

The light condensing cylinder 13 is in the form of such a cylindrical or hollow shape that an end on the side facing the light source lamp 11 is open. The light condensing cylinder 13 is disposed so that its longitudinal axis is aligned with the optical axis of the illuminating light radiated from the lamp 11. A condenser lens 21 is fixed to the open end of the light condensing cylinder 13.

The light condensing cylinder 13 is fitted within the support cylinder 14 such that it is silidable along the longitudinal axis. The support cylinder 14 is loaded with a compressive coil spring 22 that urges the light condensing cylinder 13 in a forward direction (to come closer to the lightguide connector 3).

A key slot 23 is formed in the inner peripheral surface of the support cylinder 14 and a pin 24 is erected in the outer peripheral surface of the light condensing cylinder 13. The pin 24 is in engagement with the key slot 23 to ensure that the light condensing cylinder 13 will not rotate relative to the support cylinder 14.

A connector receptacle 20 is formed at the center of the front end wall of the light condensing cylinder 13 to define a tapered hole that progressively decreases in diameter in a direction toward the lamp 11. The distal end portion of the lightguide connector 3 is formed as a tapered rod that fits into the connector receptacle 20.

The light source lamp 11 comprises a light-emitting bulb 11a and a concave reflector mirror 11b. The illuminating light issued from the lamp 11 is composed of generally parallel rays, which are allowed to converge with the condenser lens 21 so that they are focused near the position in which they are entered into the connector receptacle 20.

Therefore, the position of the focal point (at which the illuminating light is condensed) with respect to the connector receptacle 20 remains the same even if the light condensing. cylinder 13 slides relative to the support cylinder 14 along the longitudinal axis.

The lightguide fiber bundle 4 is passed through the lightguide connector 3 such that its entrance end face 4a is disposed at the distal end surface of the lightguide connector 3.

The lightguide connector 3 is inserted into the support cylinder 14 through a guide hole 19 penetrating through the front end wall of the support cylinder 14 in alignment with the longitudinal axis thereof. The inserted lightguide connector 3 has its tapered end fitted into the connector receptacle 20.

As already mentioned, the distal end portion of the lightguide connector 3 is formed as a tapered rod that fits into the connector receptacle 20 in the form of a tapered hole. Hence, the lightguide connector 3 can be inserted into and guided by the connector receptacle 20 smoothly and positively until the longitudinal axis of the lightguide connector 3 aligns with the optical axis of the illuminating light. The engagement between the lightguide connector 3 and the connector receptacle 20 compresses the coil spring 22 to absorb any dimensional errors and other factors that may potentially cause rattling.

When the distal end of the lightguide connector 3 is in engagement with the connector receptacle 20, the distal end face of the lightguide connector 3 (namely, the entrance end face 4a of the lightguide fiber bundle 4) is situated in a position where the rays of illuminating light that were allowed to converge with the condenser lens 21 are past the focal point to become slightly divergent (see FIG. 1).

Stated more specifically, the size of the rays of illuminating light in the position of the distal end face of the lightguide connector 3 is substantially identical to the size of the entrance end face 4a of the lightguide fiber bundle 4 so that the rays of illuminating light are incident on said entrance end face 4a to cause neither surplus nor deficiency. To this end, the length A of the taper forming the distal end of the lightguide connector 3 is set depending upon the size of the entrance end face 4a.

Figure 2:
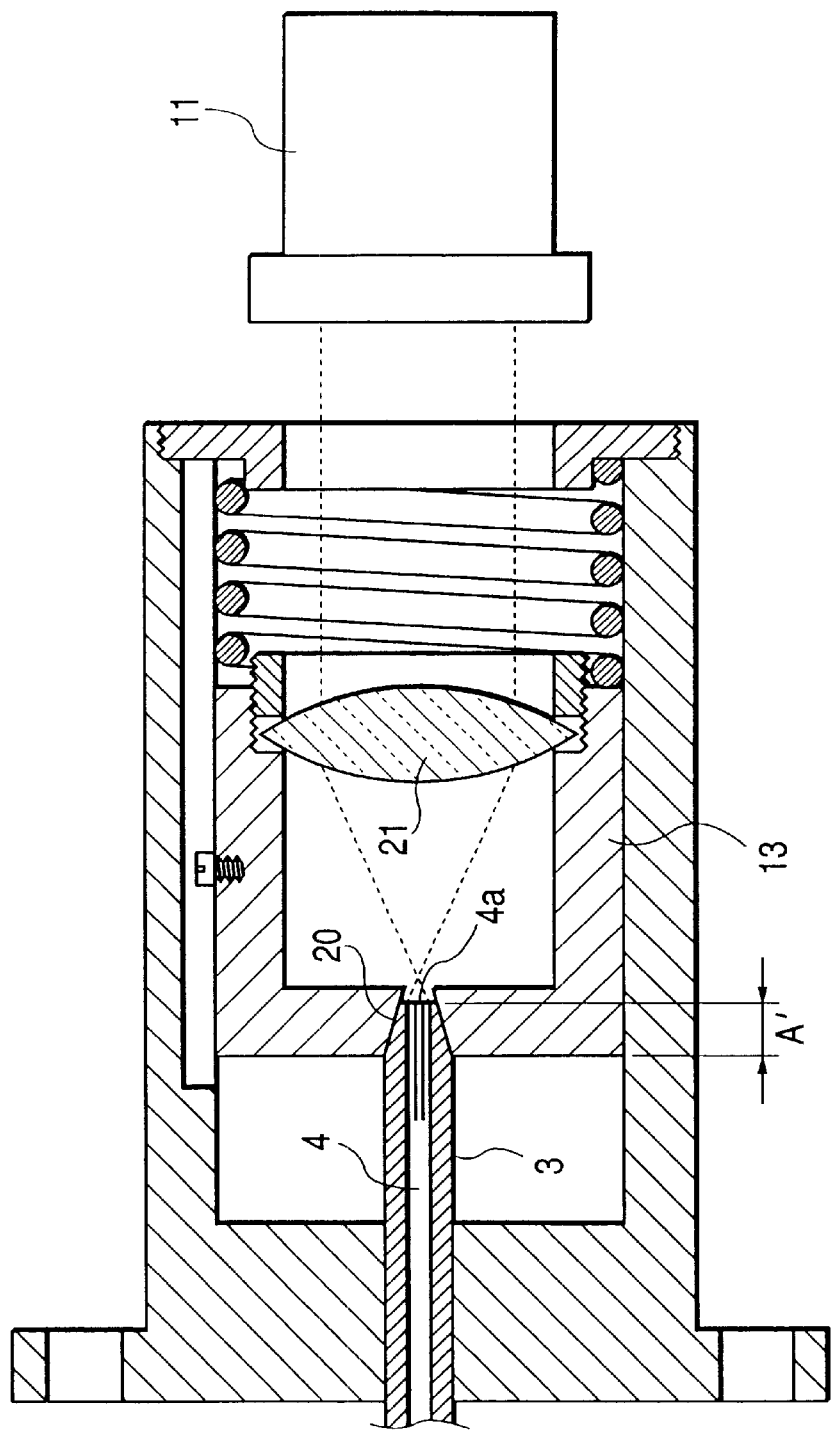
FIG. 2 is a longitudinal section of the joint between the lightguide connector of a different endoscope model and a light source apparatus according to the first embodiment of the invention.

FIG. 2 shows a different endoscope model than that shown in FIG. 1. The endoscope shown in FIG. 2 incorporates a lightguide fiber bundle 4 that consists of a smaller number of fibers and which has an entrance end face 4a of a smaller size. FIG. 2 shows a state in which the endoscope using this fiber bundle is connected to the light source apparatus 10.

Since the thickness (or size) of the entrance end face 4a of the lightguide fiber bundle 4 in the lightguide connector 3 of the model shown in FIG. 2 is smaller than that in the model shown in FIG. 1, the length A' of the taper forming the distal end of the lightguide connector 3 to be fitted into the connector receptacle 20 is set longer than the length A of the taper forming the distal end of the model shown in FIG. 1 so that the entrance end face 4a in the case of FIG. 2 is positioned closer to the focal point of the rays of illuminating light.

Thus, the lightguide connector 3 is formed in such a way that the smaller the size of the entrance end face 4a of the lightguide fiber bundle 4, the position of said entrance end face 4a is closer to the converging position of the rays of illuminating light when the lightguide connector 3 is connected to the connector receptacle 20. As a result, the rays of illuminating light are incident on the entrance end face 4a of the lightguide fiber bundle 4 without causing either surplus or deficiency and in such a position that they are substantially equal in diameter to the entrance end face 4a.

Figure 7:
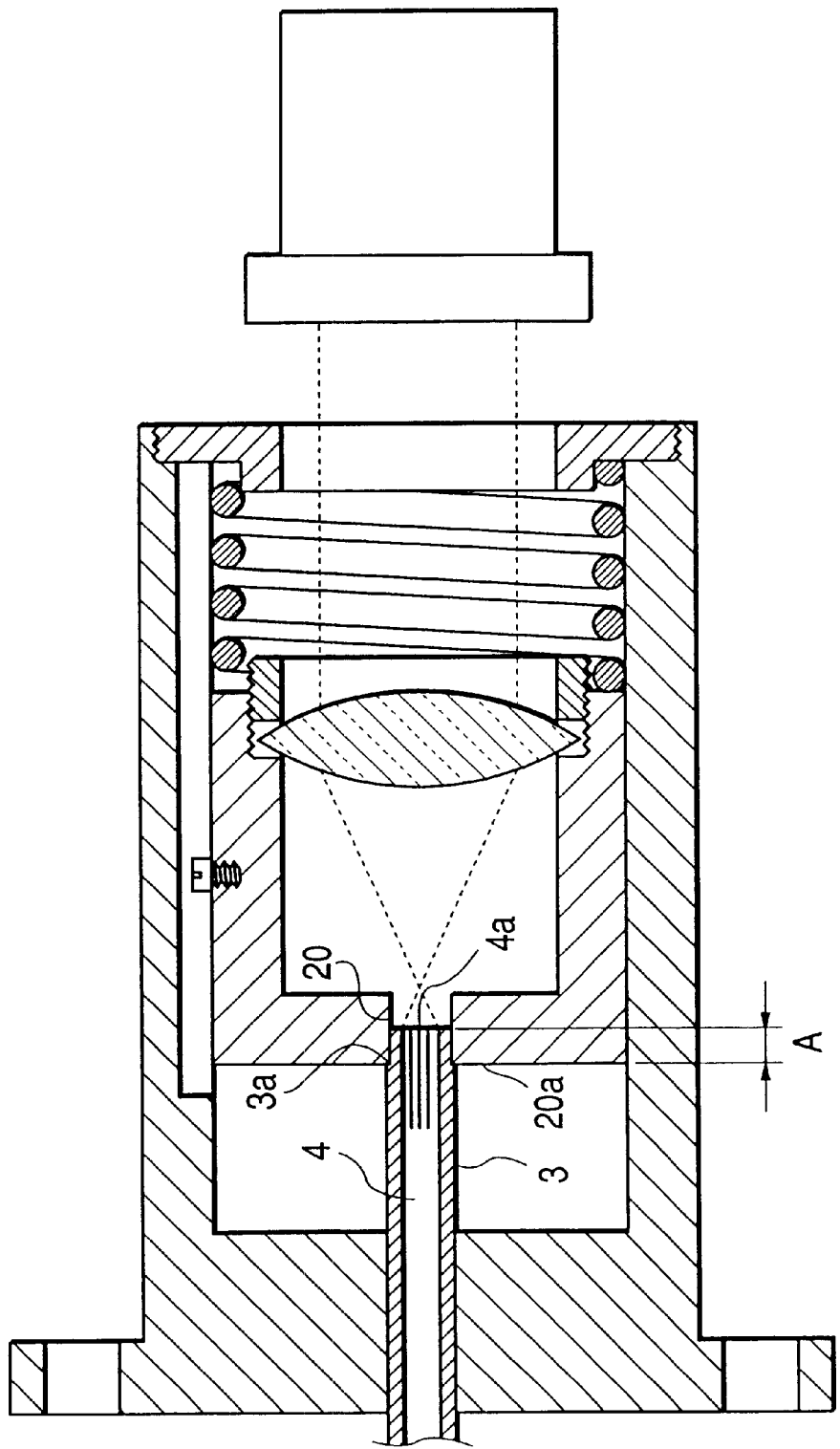
FIG. 7 is a longitudinal section of the joint between an endoscope's lightguide connector and a light source apparatus according to a second embodiment of the invention.
Figure 8:
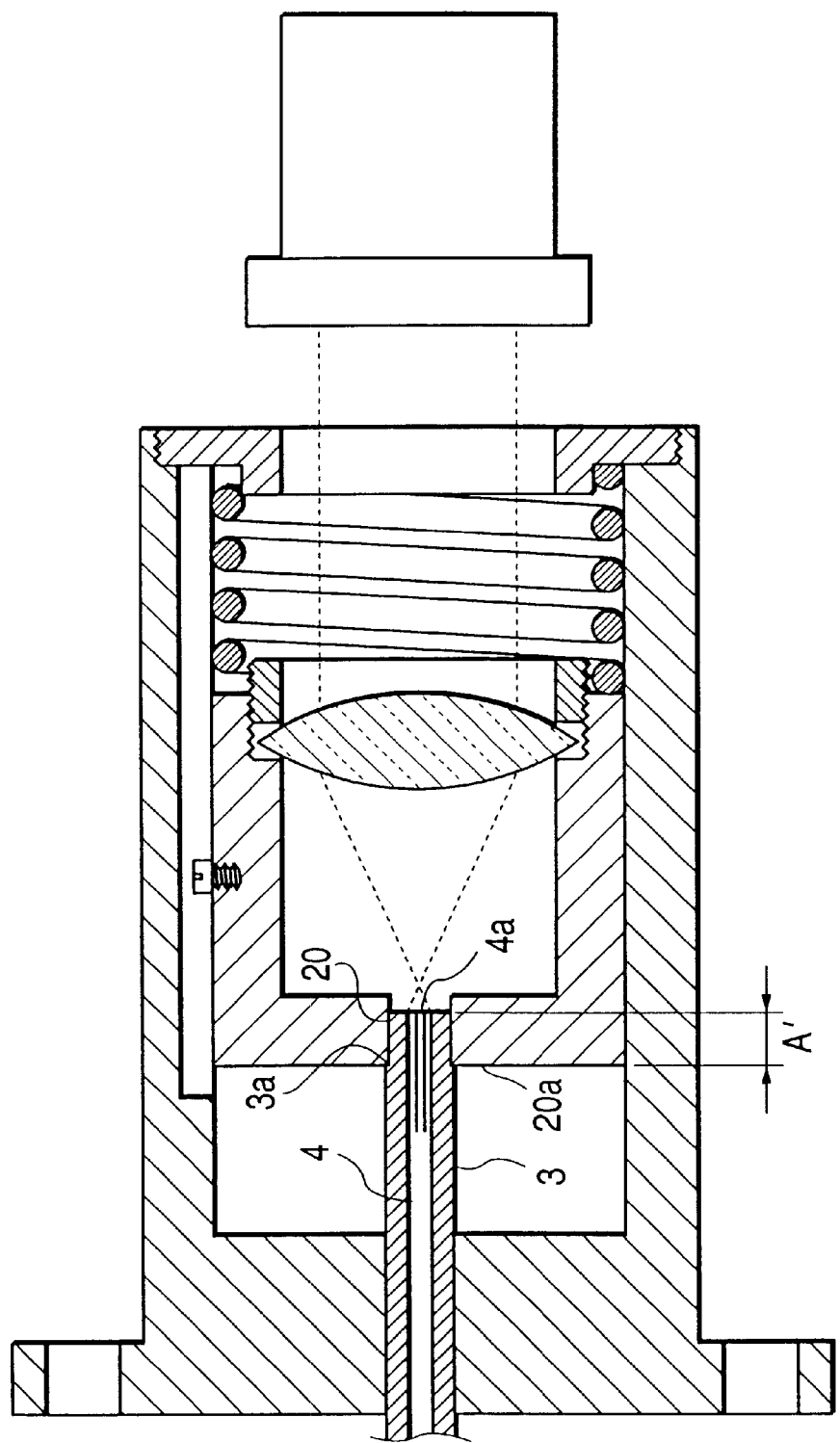
FIG. 8 is a longitudinal section of the joint between the lightguide connector of a different endoscope model and a light source apparatus according to the second embodiment of the invention.

FIGS. 7 and 8 show the second embodiment of the invention, in which the connector receptacle 20 is shaped in the form of a non-tapered hole that does not change in diameter, and a step (or stopper) 3a is formed on the lightguide connector 3 to contact the entrance rim 20a of the connector receptacle 20 (the entrance rim 20a providing a reference position). A portion of the lightguide connector 3, which extends forwardly from the step (stopper) 3a to the distal end thereof and which is to be received by the connector receptacle 20 is formed into a cylindrical shape. The stopper 3 in this embodiment is formed as a diameter expanded portion which is larger in diameter than the cylindrical portion extending between the step 3a and the distal end thereof. Similarly to the first embodiment, the distance (A, A') of the cylindrical portion extending between the step 3a and the distal end thereof is set in accordance with the size of the entrance end face 4a (A<A').

Even in that case, the distances A and A' from the step 3a on the lightguide connector 3 to the entrance end face 4a of the lightguide fiber bundle 4 are set for different endoscope models in accordance with the size of said entrance end face 4a such that the size of the rays of illuminating light at the position of the distal end face of the lightguide connector 3 is substantially identical to the size of the entrance end face 4a, whereby the rays of illuminating light can be entered into said entrance end face 4a without causing either surplus or deficiency.

According to the invention, the shape and dimensions of the lightguide connector are determined in accordance with the size of the entrance end face of the lightguide such that as the the size of said entrance end face is smaller, the position of said entrance end face is closer to the converging position of the rays of illuminating light when the lightguide connector is connected to the connector receptacle. This makes the invention compatible with various endoscope models using lightguides with different thicknesses of entrance end face and ensures that the rays of illuminating light radiated from a light source are incident on the lightguide to cause neither surplus nor deficiency, thereby achieving satisfactory illumination with high efficiency.

What is claimed is:

1. An endoscopic system, comprising:
    a light source apparatus having a built-in light source;
    a lightguide connector provided in said light source apparatus; and
    a connector receptacle provided in said light source apparatus, an entrance end face of an illuminating lightguide of an endoscope being located at a distal end face of said lightguide connector, wherein a shape and a dimension of said lightguide connector are determined in accordance with a size of said entrance end face of said illuminating lightguide, such that as the size of said entrance end face decreases, a position of said entrance end face that is established when said lightguide connector is connected to said connector receptacle is closer to a converging position of rays of illuminating light emitted from the light source, said lightguide connector being selectively attachable to said light source apparatus so that said lightguide connector is selectively attachable and detachable from said connector receptacle.

2. The endoscopic system of claim 1, wherein said connector receptacle is shaped in a form of a tapered hole that progressively decreases in diameter in a direction toward said light source, whereas a distal end portion of said lightguide connector is shaped in a form of a tapered rod that fits into said connector receptacle.

3. The endoscopic system of claim 1, wherein when said lightguide connector is connected to said connector receptacle, a stopper formed on said lightguide connector contacts a reference position formed on said connector receptacle side and a distance from a contact position to the entrance end face of said lightguide is determined in accordance with the size of said entrance end face.

4. The endoscopic system of claim 1, further comprising a ventilation window, provided in a lens unit incorporating a lens for converging rays of illuminating light emitted from said light source, that cools a distal end portion of said lightguide connector.

5. The endoscopic system of claim 1, further comprising a lens to converge rays from said built-in light source that is affixed to said connector receptacle.

6. The endoscopic system of claim 1, wherein an optical axis direction insertion amount of said lightguide connector with respect to said connector receptacle is set in accordance with a size of an incident surface size of said lightguide.

7. Plural lightguide connectors connected to respective endoscopes and adapted to be individually connected to a single light source apparatus having a light condensing element defining a fixed focal point with respect to a connector receptacle, wherein:
    a first lightguide connector supports a first lightguide, a light entrance end face of said first lightguide being exposed at a distal end of said first lightguide connector and having a first diameter;
    a second lightguide connector supports a second lightguide, a light entrance end face of said second lightguide being exposed at a distal end of said second lightguide connector and having a second diameter that is smaller than said first diameter of said first lightguide; and
    a distance between said light entrance end face of said first lightguide and said focal point defined when said first lightguide connector is received by said connector receptacle is larger than a distance between said light entrance end face of said second lightguide and said focal point defined when said second lightguide connector is received by said connector receptacle, said first lightguide connector and said second lightguide connector being selectively attachable to said single light source apparatus so that each of said first lightguide connector and said second lightguide connector are selectively attachable and detachable from said connector receptacle.

8. The plural lightguide connectors of claim 7, wherein a portion of said first lightguide connector, which is received by said connector receptacle, is smaller in length than a portion of said second lightguide connector, which is received by said connector receptacle.

9. The plural lightguide connectors of claim 8, wherein each of said portions of said first lightguide connector and said second lightguide connector is tapered.

10. The plural lightguide connectors of claim 8, wherein each of said portions of said first lightguide connector and said second lightguide connector is cylindrical, said first lightguide connector and said second lightguide connector having diameter-expanded portions adjacent to and contiguous with said cylindrical portions, respectively.

11. A lightguide connector joint for an endoscopic system, in which an entrance end face of an illuminating lightguide of an endoscope is located at a distal end face of a lightguide connector, said lightguide connector and a connector receptacle to which said lightguide connector is to be connected being provided in a light source apparatus side having a built-in light source, wherein:

a shape and a dimension of said lightguide connector are determined in accordance with a size of the entrance end face of said lightguide such that as the size of said entrance end face is smaller, a position of said entrance end face that is established when said lightguide connector is connected to said connector receptacle is closer to a converging position of rays of illuminating light emitted from the light source, said lightguide connector being selectively attachable to said light source apparatus so that said lightguide connector is selectively attachable and detachable from said connector receptacle.

12. The lightguide connector joint for an endoscopic system as recited in claim 11, wherein said connector receptacle is shaped in a form of a tapered hole that progressively decreases in diameter in a direction toward said light source, whereas a distal end portion of said lightguide connector is shaped in a form of a tapered rod that fits into said connector receptacle.

13. The lightguide connector joint for an endoscopic system as recited in claim 11, wherein when said lightguide connector is connected to said connector receptacle, a stopper formed on said lightguide connector contacts a reference position formed on said connector receptacle side and a distance from a contact position to the entrance end face of said lightguide is determined in accordance with the size of said entrance end face.

14. The lightguide connector joint for an endoscopic system as recited in claim 11, further comprising a ventilation window, provided in a lens unit incorporating a lens for converging rays of illuminating light emitted from said light source unit, that cools a distal end portion of said lightguide connector.

* * * * *